(12) United States Patent  
Afzal (10) Patent No.: US 6,210,365 B1
(45) Date of Patent: Apr. 3, 2001

(54) PERFUSION CATHETER SYSTEM HAVING SUTURELESS ARTERIOTOMY SEAL AND METHODS OF USE

(75) Inventor: Thomas A. Afzal, Menlo Park, CA (US)

(73) Assignee: Cardiovention, Inc., Santa Clara, CA (US)

( * ) Notice: Subject to any disclaimer, the term of this patent is extended or adjusted under 35 U.S.C. 154(b) by 0 days.

(21) Appl. No.: 09/134,280

(22) Filed: Aug. 14, 1998

(51) Int. Cl.[7] .................................................. A61M 29/00
(52) U.S. Cl. ..................... 604/101.03; 604/4.01; 604/96.01; 604/101.01; 604/101.05; 604/102.01; 604/103.01; 604/104; 604/115; 604/164.01; 604/532; 604/538; 606/194; 600/435
(58) Field of Search .................... 604/96–97, 204, 604/45, 101–104, 115, 131, 164, 264, 272, 274, 532–33, 538–39, 523–24, 528; 128/898; 600/433–35; 606/191–92, 194–95, 198

(56) References Cited

U.S. PATENT DOCUMENTS

| 3,482,575 | * | 12/1969 | Claff et al. .............................. 604/4 |
| 3,516,412 | * | 6/1970 | Ackerman ............................ 128/418 |
| 3,769,960 |   | 11/1973 | Robinson ............................. 128/1 D |
| 3,833,003 |   | 9/1974 | Taricco ............................... 128/347 |
| 3,952,742 | * | 4/1976 | Taylor ................................. 604/101 |
| 4,352,358 |   | 10/1982 | Angelchik ....................... 128/334 R |
| 4,366,819 |   | 1/1983 | Kaster .............................. 128/334 C |
| 4,368,736 |   | 1/1983 | Kaster .............................. 128/334 C |
| 4,527,549 | * | 7/1985 | Gabbay ............................... 604/101 |
| 4,705,507 |   | 11/1987 | Boyles ............................... 604/101 |
| 4,784,639 | * | 11/1988 | Patel ................................... 604/53 |
| 4,836,204 | * | 6/1989 | Landymore et al. ................ 604/101 |
| 4,976,261 | * | 12/1990 | Gluck et al. ..................... 128/207.15 |
| 5,106,381 | * | 4/1992 | Chikama ............................. 604/523 |
| 5,167,628 |   | 12/1992 | Boyles ............................... 604/101 |
| 5,188,619 |   | 2/1993 | Myers ................................. 604/280 |
| 5,312,341 | * | 5/1994 | Turi ...................................... 604/96 |
| 5,312,343 | * | 5/1994 | Krog et al. .......................... 604/101 |
| 5,312,344 |   | 5/1994 | Grinfeld et al. ..................... 604/101 |
| 5,409,019 | * | 4/1995 | Wilk .................................... 128/898 |
| 5,423,744 | * | 6/1995 | Gencheff et al. ..................... 604/53 |
| 5,433,700 |   | 7/1995 | Peters ..................................... 604/4 |
| 5,556,412 |   | 9/1996 | Hill ..................................... 606/194 |
| 5,558,644 | * | 9/1996 | Boyd et al. ............................ 604/96 |
| 5,695,457 |   | 12/1997 | St. Goar et al. ........................ 604/4 |
| 5,728,068 | * | 3/1998 | Leone et al. ........................ 604/101 |
| 5,772,632 | * | 6/1998 | Forman ............................... 604/101 |
| 5,782,800 | * | 7/1998 | Yoon .................................... 604/54 |
| 5,792,094 | * | 8/1998 | Stevens et al. ......................... 604/4 |
| 5,800,393 | * | 9/1998 | Sahota ................................... 604/96 |
| 5,810,757 | * | 9/1998 | Sweezer, Jr. et al. .................. 604/4 |
| 5,829,447 | * | 11/1998 | Stevens et al. ...................... 128/898 |

* cited by examiner

Primary Examiner—Angela D. Sykes
Assistant Examiner—Patricia Bianco
(74) Attorney, Agent, or Firm—Fish & Neave; Nicola A. Pisano (57) ABSTRACT

Apparatus and methods are provided for delivering oxygenated blood to a patient undergoing cardiac surgery using a perfusion catheter having a distal end carrying first and second sealing members. When the perfusion catheter is inserted through an arteriotomy site, the first and second sealing members are disposed to engage opposite surfaces of a thickness of a vessel to apply pressure against the opposite surfaces of the thickness to seal blood perfused into the vessel from leaking through the arteriotomy site. Apparatus for placing the perfusion catheter, and methods of using the apparatus also are provided.

30 Claims, 4 Drawing Sheets

PERFUSION CATHETER SYSTEM HAVING SUTURELESS ARTERIOTOMY SEAL AND METHODS OF USE

FIELD OF THE INVENTION

The present invention relates to catheters used to return oxygenated blood from a cardiopulmonary bypass machine to a patient during cardiac surgery. More specifically, the present invention relates to a perfusion catheter, and methods of use, that enable the catheter to be intraoperatively placed in the aorta using a sutureless arteriotomy seal.

BACKGROUND OF THE INVENTION

Each year hundreds of thousands of people are afflicted with vascular diseases, such as arteriosclerosis, that result in cardiac ischemia. For more than thirty years, such disease, especially of the coronary arteries, has been treated using open surgical procedures, such as coronary artery bypass grafting. During such bypass grafting procedures, a sternotomy is performed to gain access to the pericardial sac, the patient is put on cardiopulmonary bypass, and the heart is stopped using a cardioplegia solution.

More recently, techniques are being developed, for example, by Heartport, Inc., Redwood City, Calif., that permit cardiac surgery using an endoscopic approach, in which small access openings are created between the ribs. The bypass graft or heart valve repair procedure is performed guided by an image displayed on a video monitor. In the "keyhole" techniques developed by Heartport, the patient's heart is stopped and the patient is placed on cardiopulmonary bypass. Still other techniques being developed, for example, by CardioThoracic Systems, Inc., of Cupertino, Calif., enable such bypass graft procedures to be performed on a beating heart.

In those techniques that involve stopping the heart to perform surgery, blood flow to the heart is occluded, for example, by placing occlusion balloons in the ascending aorta and/or the vena cava. Venous blood is then withdrawn from the patient, for example, from the vena cava, and oxygenated using an extracorporeal oxygenation circuit. The oxygenated blood is perfused into the patient in the vicinity of the aortic arch to provide oxygenated blood to the brain, internal organs and extremities.

U.S. Pat. No. 5,312,344 to Grinfeld et al. describes a multi-lumen perfusion catheter for perfusing oxygenated blood into a patient on cardiopulmonary bypass. The catheter has a distal balloon for occluding the ascending aorta, a first lumen for delivering cardioplegia solution through a first opening distal to the balloon, and a second lumen for perfusing oxygenated blood through a second opening proximal to the balloon. The catheter may be positioned in the ascending aorta either intraoperatively through an opening in the aorta, or in a retrograde manner via a femoral artery and the abdominal aorta.

One drawback associated with recently developed keyhole methods of cardiac surgery is that the surgeon often has only limited room in which to maneuver. This, in turn, may render previously known apparatus too cumbersome to be effectively used in conjunction with such techniques. Thus, for example, while the intraoperative version of the catheter described in the foregoing patent to Grinfeld et al. may be used instead of a cross-clamp where a sternotomy has been performed, the device may be less useful when keyhole surgical techniques are employed.

Specifically, intraoperative placement of the foregoing catheter involves placing a purse-string suture surrounding the arteriotomy, to prevent excessive blood loss. Because there may be insufficient room in which to form a purse string suture in a keyhole-type procedure, the surgeon may be unable to provide a tight seal around the entry point of the catheter.

It therefore would be desirable to provide apparatus and methods for delivering oxygenated blood to a patient from a cardiopulmonary bypass machine that overcome the drawbacks of previously known perfusion catheters.

It further would be desirable to provide apparatus and methods that enable a perfusion catheter to be positioned in the aorta via a sutureless arteriotomy.

A number of devices and methods have been developed to provide sutureless anastomoses. U.S. Pat. Nos. 4,366,819 and 4,368,736, both to Kaster, describe assemblies that provide sutureless anastomosis of a bypass graft by capturing the graft material between an interior flange and an exterior ring. U.S. Pat. No. 4,352,358 to Angelchik describes an anastomosis device formed from a tubular elastic membrane that is expanded on either side of the entry wound to provide a sutureless seal. None of these previously known devices appear suitable, without extensive modification, for providing a temporary sutureless arteriotomy for a perfusion catheter.

U.S. Pat. No. 5,167,628 to Boyles describes a catheter for isolating the coronary ostium between two toroidal-shaped balloons. The catheter includes a lumen enabling blood to pass from the left ventricle to the ascending aorta, while the balloons define a chamber into which treatment material may be provided to the coronary arteries. The patent describes that the balloons are spaced apart so that the lower balloon is disposed beneath the aortic valve in the left ventricle and the upper balloon is positioned distal of the coronary arteries.

In view of the foregoing, it would be desirable to provide apparatus and methods for delivering oxygenated blood to a patient from a cardiopulmonary bypass machine using sealing members that provide a sutureless arteriotomy, with little or no blood leakage.

It further would be desirable to provide apparatus and methods for occluding the aorta and for providing cardioplegia solution to the aortic root using a perfusion catheter inserted via a sutureless arteriotomy.

SUMMARY OF THE INVENTION

In view of the foregoing, it is an object of this invention to provide apparatus and methods for delivering oxygenated blood to a patient from a cardiopulmonary bypass machine, and that overcome the drawbacks of previously known perfusion catheters.

It is a further object of the present invention to provide apparatus and methods that enable a perfusion catheter to be positioned in the ascending aorta via a sutureless arteriotomy.

It is another object of this invention to provide apparatus and methods for delivering oxygenated blood to a patient from a cardiopulmonary bypass machine using sealing members that provide a sutureless arteriotomy, with little or no blood leakage.

It is a further object of the present invention to provide apparatus and methods for occluding the aorta and for providing cardioplegia solution to the aortic root using a perfusion catheter inserted via a sutureless arteriotomy.

These and other objects of the invention are accomplished by providing a perfusion catheter having a distal end carrying first and second sealing members. When the perfusion catheter is inserted through an arteriotomy site, the first and second sealing members are disposed to engage opposite surfaces of a thickness of a vessel wall. When disposed across a vessel wall, the first and second sealing members capture the intervening tissue and apply pressure against the opposite surfaces of the thickness of the vessel wall to seal blood perfused into the aorta from leaking through the arteriotomy site.

In one embodiment, the perfusion catheter includes a multi-lumen catheter having first and second toroidal balloons defining first and second sealing members, a third balloon for occluding the aorta, a lumen for providing oxygenated blood to the aorta, and a lumen for injecting cardioplegia solution into the aortic root, proximal of the occlusion balloon. Alternatively, the third balloon and cardioplegia injection lumen may be carried on a separate catheter that is inserted through a lumen of the perfusion catheter. The distal region of the catheter also may include a member that biases the perfusion catheter into a preferred delivery shape when deployed, e.g., with the axis of a blood flow outlet port coinciding with the axis of the aorta. A stylet for forming the arteriotomy puncture and inserting the perfusion catheter also is provided.

In an alternative embodiment, the perfusion catheter comprises a multi-lumen catheter having an inner shaft including a toroidal balloon defining a first sealing member, an occlusion balloon for occluding the aorta, a lumen for providing oxygenated blood to the aorta, and a lumen for injecting cardioplegia solution into the aortic root, proximal of the occlusion balloon. An outer shaft is disposed for movement in the proximal and distal directions on the inner shaft and includes an elastomeric flange or toroidal balloon defining a second sealing member. Once the first balloon is positioned and inflated, the outer shaft is advanced in the distal direction to engage the tissue disposed therebetween and seal the arteriotomy.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

The present invention provides a perfusion catheter that may be positioned in a patient's aorta without suturing the arteriotomy site, and with little or no leakage. Specifically, perfusion catheters constructed in accordance with the principles of the present invention include first and second sealing members disposed on the catheter shaft in closely spaced relation that sealingly capture the edge of the arteriotomy site. In addition, the perfusion catheters of the present invention may include an inflatable occlusive member for occluding retrograde flow of blood into the heart, a lumen for delivering cardioplegia solution to the aortic root, and an element that causes the distal end of the perfusion catheter to conform to the vessel.

Figure 1:
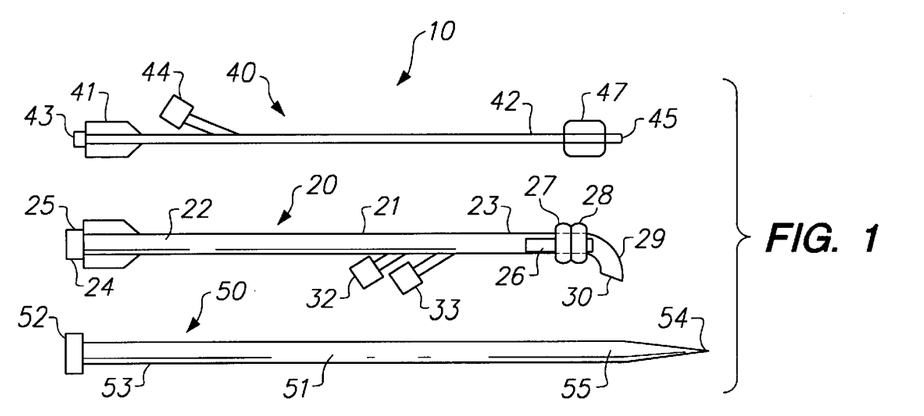
FIG. 1 is a side view of an illustrative embodiment of a perfusion catheter system constructed in accordance with the present invention.
Figure 2:
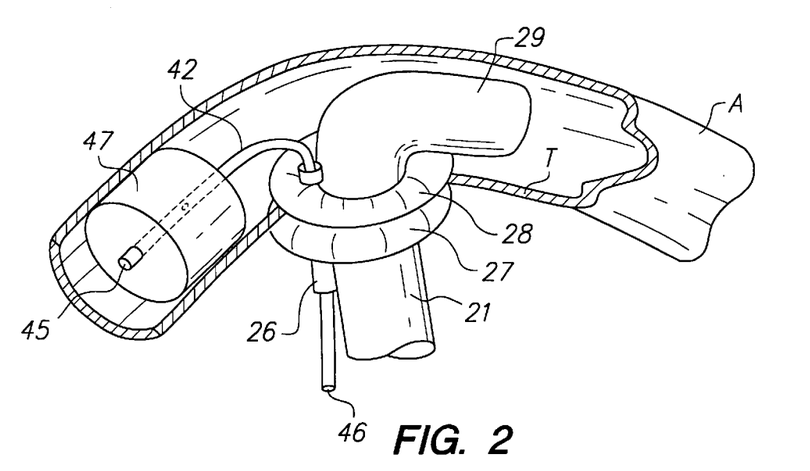
FIG. 2 is a perspective view of the distal end of the perfusion catheter system of FIG. 1 disposed in a patient's aortic arch.
Figure 3:
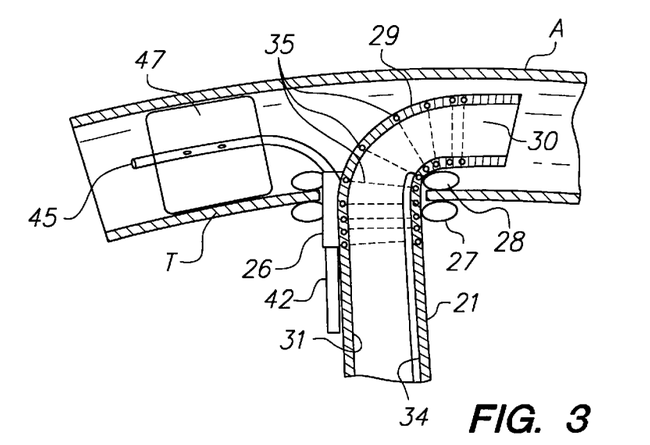
FIG. 3 is a side-sectional view of the distal end of the perfusion catheter system of FIG. 2.

Referring to FIGS. 1 to 3, an illustrative perfusion catheter system constructed in accordance with the principles of the present invention is described. Catheter system 10 comprises perfusion catheter 20, balloon catheter 40 and stylet 50.

Perfusion catheter 20 comprises flexible tube 21 having proximal end 22 and distal end 23. Proximal end 22 includes fitting 24 for coupling blood flow inlet port 25 to an outlet of a cardiopulmonary bypass machine (not shown). Distal end 23 includes tube 26, closely-spaced together sealing members 27 and 28, and curved region 29 having blood flow outlet port 30. Lumen 31 (see FIG. 3) extends from blood flow inlet port 25 to blood flow outlet port 30. Tube 26 is affixed to the exterior surface of perfusion catheter 20 and forms a guide lumen for balloon catheter 40, as described hereinbelow. Sealing members 27 and 28 comprise toroidal balloons, and are coupled to inflation ports 32 and 33, respectively, via separate lumens 34 disposed within lumen 31. Inflation ports 32 and 33 may be coupled to syringes (not shown) filled with an inflation medium, such as saline, to selectively inflate the balloons.

Perfusion catheter 20 preferably comprises a material typically used in catheter construction, such as polyethylene, polyvinylchloride, or polyurethane. Curved region 29 preferably includes pre-formed metal alloy spring 35 embedded in its thickness (see FIG. 3). Spring 35 flexes from a substantially straight shape, when perfusion catheter 20 is disposed over stylet 50, to a curved shape that conforms to the arch of the aorta, as shown in FIGS. 2 and 3. Sealing members 27 and 28 may comprise a compliant, semi-compliant, or non-compliant material, and more preferably, a non-compliant or semi-compliant material. Tube 26 may include a thin seal of a plastic material, e.g., polyethylene, which is punctured when balloon catheter 40 is inserted through the tube.

Balloon catheter 40 has proximal end 41 and distal end 42. Proximal end 41 includes cardioplegia inlet port 43 and inflation port 44. Distal end 42 includes outlet port 45 coupled via lumen 46 (see FIG. 3) to cardioplegia inlet port 43, and balloon 47 coupled via a lumen to inflation port 44. Balloon catheter 40 has a diameter selected so that distal end 42 passes through tube 26 of perfusion catheter 20 when balloon 47 is deflated, and may include one or more additional lumens, for example, for venting the aortic root. Balloon catheter 40 preferably comprises a material typically used in catheter construction, such as polyethylene, polyvinylchloride, or polyurethane, while balloons 47 may comprise a compliant, semi-compliant, or non-compliant material, and more preferably, a compliant material.

Stylet 50 comprises elongated shaft 51 having knob 52 at proximal end 53 and sharpened non-coring tip 54 at distal end 55. Stylet 50 is sized to slidingly fit within lumen 31 of perfusion catheter 20, and may comprise a catheter type material, such as described hereinabove. Stylet 50 may include grooves in its outer surface to accommodate the presence of lumens 34 in lumen 31 of perfusion catheter 20. In addition, tip 55 may include a sharpened metal alloy tip embedded in distal end 55 to enhance the cutting ability of the stylet.

Referring now to FIGS. 2 and 3, when perfusion catheter 20 is positioned within a vessel, preferably aorta A, for example, during keyhole cardiac surgery, curved region 29 conforms to the curve of the aorta. Sealing member 28 is disposed within aorta A and contacts the interior surface of tissue T of the vessel wall. Sealing member 27 is disposed outside aorta A and contacts the exterior surface of tissue T of the vessel wall. When sealing members 27 and 28 are inflated, e.g., when the surgeon injects a suitable inflation medium in sealing members 27 and 28 via inflation ports 32 and 33, the balloons expand to bear against opposite surfaces of the thickness of tissue T. Sealing members 27 and 28 thereby occlude and seal the arteriotomy site against leakage, without the need to place a purse string suture around the catheter.

Balloon catheter 40 is advanced through tube 26 along a guide wire, and balloon 47 is inflated using a suitable inflation medium to occlude the aorta. Cardioplegia solution then may be injected through cardioplegia inlet port 43, lumen 46 and cardioplegia outlet port 45 into the aortic root to stop the heart and perfuse the coronary arteries.

Figures 4A, 4B, 4C:
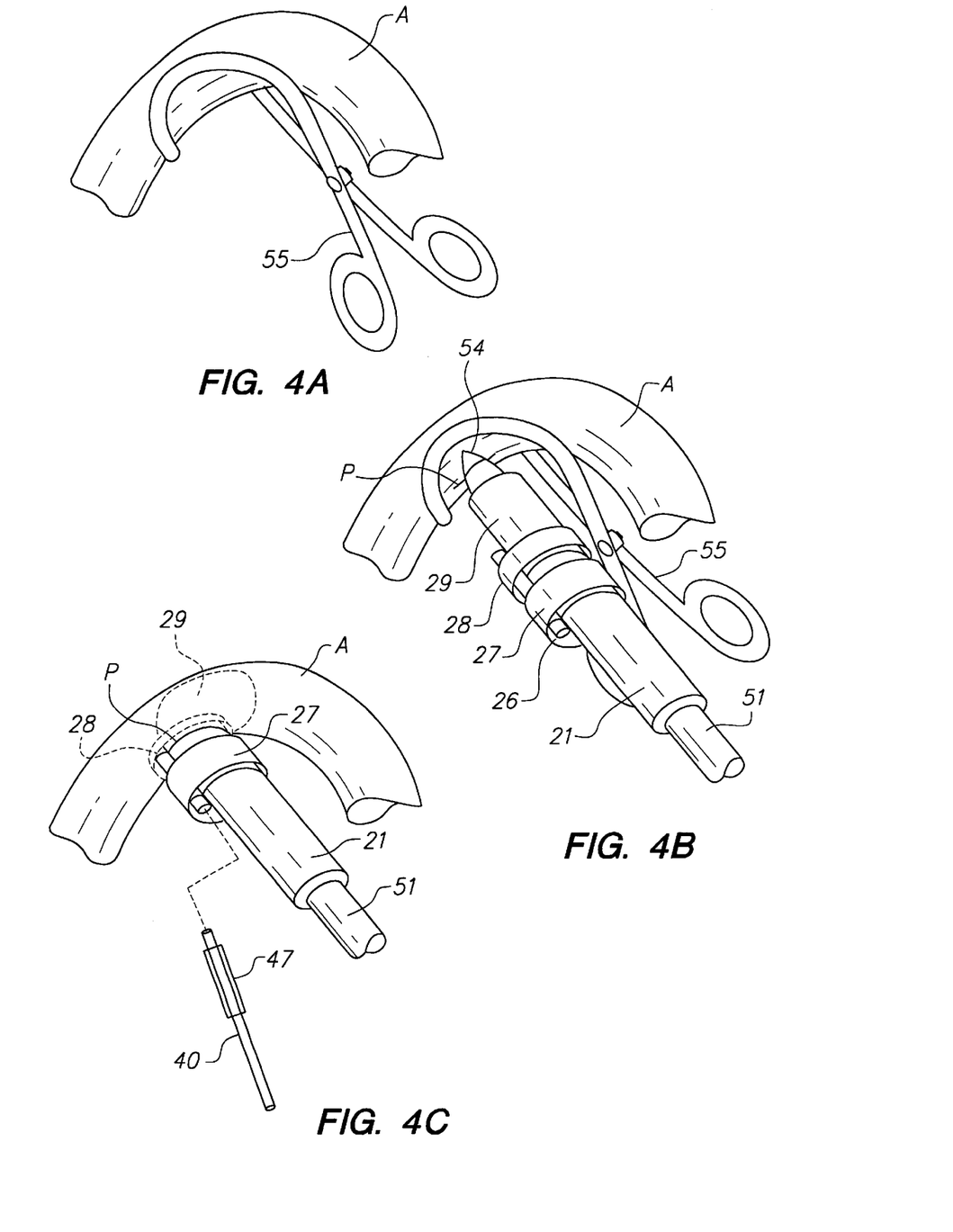
FIGS. 4A to 4C illustrate a method of placing the distal end of the perfusion catheter of FIG. 1 in an aortic arch.
Figure 5:
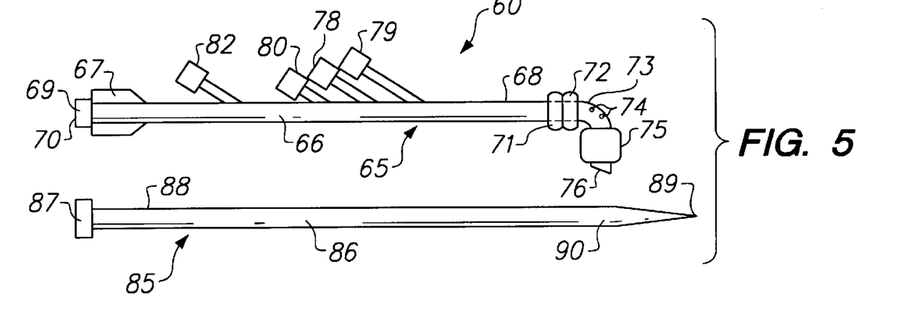
FIG. 5 is a side view of an alternative embodiment of a perfusion catheter system constructed in accordance with the present invention.

Referring now to FIGS. 4A to 4C, a method of intraoperatively using perfusion catheter system 10 of the present invention to perfuse a patient undergoing cardiac surgery with oxygenated blood is described. As shown in FIG. 4A, a portion of aorta A is first partially clamped using previously known forceps-type cross-clamp 55 to isolate a region in which the arteriotomy is to be performed.

Perfusion catheter 20 is placed over stylet 50 so that tip 54 extends out of blood flow outlet port 30. Sealing members 27 and 28 are folded, and preferably pre-folded, flat against the exterior of perfusion catheter 20 so as to minimize the insertion profile of the catheter. Perfusion catheter 20 and stylet 50 are disposed adjacent to the isolated region of the aorta, and the stylet is advanced to create puncture P in the vessel wall, as shown in FIG. 4B. Perfusion catheter 20 is then advanced over distal end 55 of the stylet with the stylet held stationary.

As the perfusion catheter is inserted into the aorta through puncture P, spring 35 causes curved region 29 to revert to its curved shape, thus allowing the perfusion catheter to be placed in the aorta without contacting the opposing wall of the vessel, as shown in FIG. 4C. Sealing members 27 and 28 then are inflated (only sealing member 28 is shown inflated in FIG. 4C), until the balloons contact the opposite surfaces of the intervening thickness of the vessel wall (see FIG. 3).

Once sealing members 27 and 28 have been inflated to seal puncture P, balloon catheter 47 is inserted through tube 26 and directed in a retrograde fashion, for example, using a guide wire inserted through lumen 46 and cardioplegia outlet port 45 of balloon catheter 40. Balloon 47 then is inflated to occlude the aorta upstream of blood flow outlet port 30 of perfusion catheter 20. Stylet 50 is removed from lumen 31, and blood flow inlet port 25 is coupled to an outlet of a cardiopulmonary bypass machine to perfuse aorta A, while cardioplegia solution is injected through lumen 46 of balloon catheter 40.

Referring now to FIGS. 5 to 8, an alternative embodiment of a perfusion catheter system constructed in accordance with the principles of the present invention is described. Catheter system 60 comprises perfusion catheter 65 and stylet 85.

Perfusion catheter 65 comprises flexible tube 66 having proximal end 67 and distal end 68. Proximal end 67 includes fitting 69 for coupling blood flow inlet port 70 of the perfusion catheter to an outlet of a cardiopulmonary bypass machine (not shown). Distal end 68 includes closely-spaced together sealing members 71 and 72, curved region 73 having cardioplegia outlet ports 74, occlusion balloon 75 and blood flow outlet port 76. Lumen 77 (see FIG. 7) extends from blood flow inlet port 70 to blood flow outlet port 76.

Sealing members 71 and 72, preferably balloons, and occlusion balloon 75, are coupled to inflation ports 78, 79 and 80, respectively, via separate lumens 81 disposed within lumen 77. Inflation ports 78, 79 and 80 may be coupled to syringes (not shown) filled with an inflation medium, such as saline, to selectively inflate the balloons. Cardioplegia outlet ports 74 are coupled to cardioplegia inlet port 82 via lumen 83 disposed within lumen 77.

Figure 6:
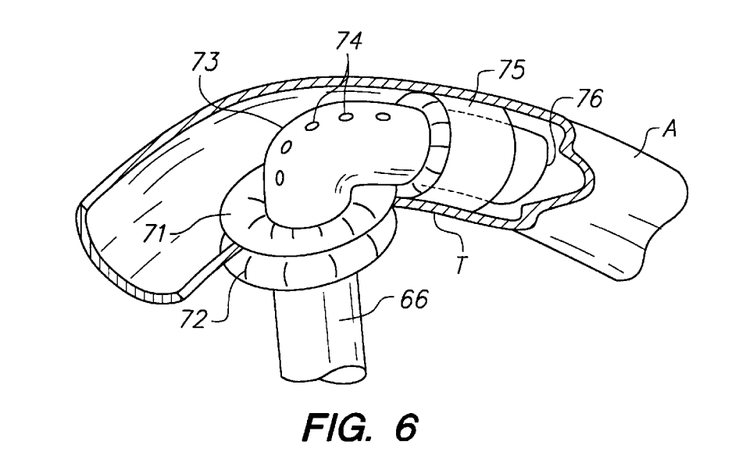
FIG. 6 is a perspective view of the distal end of the perfusion catheter system of FIG. 5 disposed in a patient's aortic arch.
Figure 7:
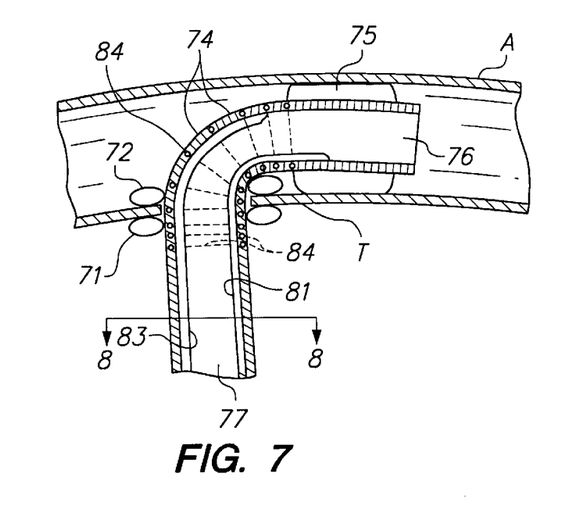
FIG. 7 is a side-sectional view of the distal end of the perfusion catheter of FIG. 6.
Figure 8:
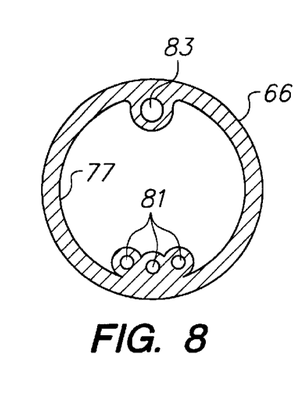
FIG. 8 is a cross-sectional view of the perfusion catheter of FIG. 5, taken along view line 8—8 of FIG. 7.

Perfusion catheter 65 preferably comprises a material, as described hereinabove with respect to the embodiment of FIGS. 1–4, and includes pre-formed metal alloy spring 84 embedded in its thickness. Spring 84 flexes from a substantially straight shape, when perfusion catheter 65 is disposed over stylet 85, to a curved shape that conforms to the arch of the aorta, as shown in FIGS. 6 and 7. Sealing members 71 and 72 and occlusion balloon 75 may comprise a compliant, semi-compliant, or non-compliant material, and more preferably, sealing members 71 and 72 comprise a non-compliant or semi-compliant material, while occlusion balloon 75 more preferably comprises a compliant material.

Stylet 85 is similar in construction to stylet 50 described hereinabove, and comprises elongated shaft 86 having knob 87 at proximal end 88 and sharpened non-coring tip 89 at distal end 90. Stylet 85 is sized to slidingly fit within lumen 77 of perfusion catheter 65, and may comprise a catheter type material, such as described hereinabove. Stylet 85 may include grooves to accommodate the presence of lumens 81 and 83, and tip 89 optionally may include a sharpened metal alloy tip embedded in distal end 90 to enhance the cutting ability of the stylet.

Referring to FIGS. 6 and 7, when perfusion catheter 65 is positioned within a vessel, preferably aorta A, curved region 73 conforms to the curve of the aorta. Sealing member 72 is disposed within aorta A and contacts the interior surface of tissue T, while sealing member 71 is disposed outside aorta A and contacts the exterior surface of tissue T. When sealing members 71 and 72 are inflated, the balloons expand to bear against the opposite surfaces of the thickness of tissue T, thus providing a sutureless arteriotomy seal for perfusion catheter 65.

Operation of catheter system 60 is similar to that described with respect to FIGS. 4A to 4C. The aorta is first partially clamped to isolate a region in which the arteriotomy is to be performed, and perfusion catheter 65 is placed over stylet 85 so that tip 89 extends out of blood flow outlet port 76. Sealing members 71 and 72 occlusion balloon 75 are pre-folded flat against the exterior of perfusion catheter 65 so as to minimize the insertion profile of the catheter. The perfusion catheter and stylet are disposed adjacent to the isolated region of the aorta, and the stylet is advanced to create a puncture in the vessel wall.

The perfusion catheter is then advanced over distal end 90 of the stylet with the stylet held stationary, so that spring 84 causes curved region 73 to revert to its curved shape as the perfusion catheter is inserted into the aorta through the puncture. Sealing members 71 and 72 are inflated until the balloons contact and bear against the intervening thickness of the vessel wall. Occlusion balloon 75 also is inflated using a suitable inflation medium, injected via inflation port 80, to occlude the aorta upstream of blood flow outlet port 76.

Stylet 85 is removed from lumen 77, and blood flow inlet port 70 is coupled to an outlet of a cardiopulmonary bypass machine to perfuse aorta A. Cardioplegia solution also may be injected through cardioplegia inlet port 82, lumen 83 and cardioplegia outlet ports 74 into the aortic root to stop the heart and perfuse the coronary arteries.

Figure 9:
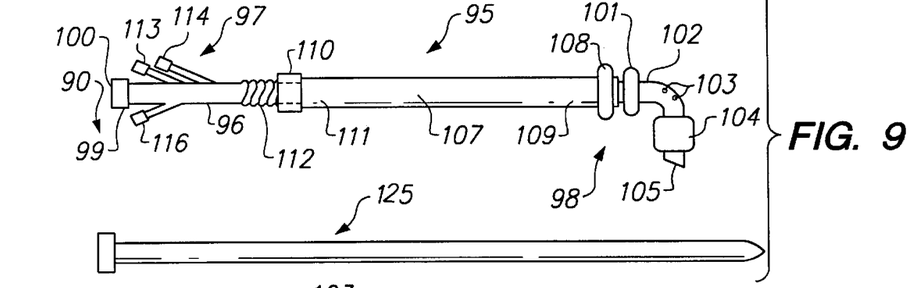
FIG. 9 is a side view of an alternative embodiment of a perfusion catheter system constructed in accordance with the present invention.
Figures 10A, 10B, 11:
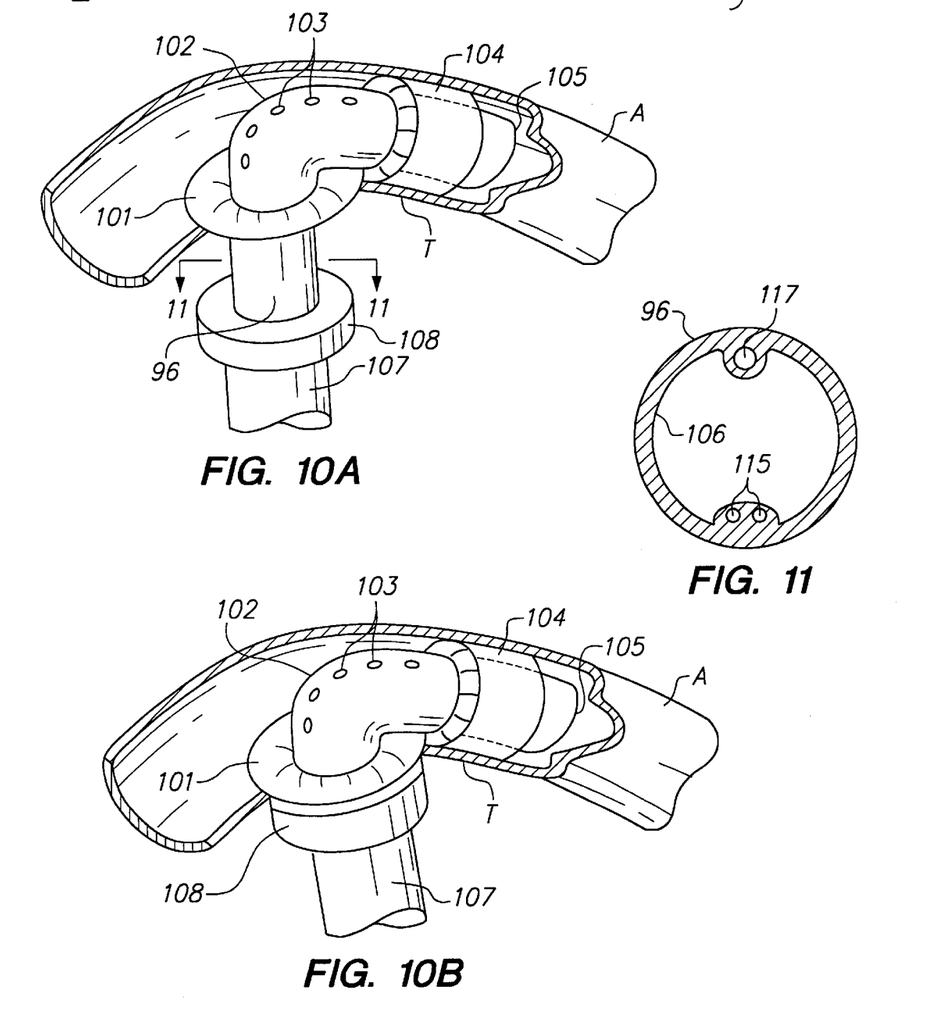
FIGS. 10A and 10B are perspective views of the distal end of the perfusion catheter system of FIG. 9 showing steps of deploying the catheter in a patient's aortic arch.
FIG. 11 is a side-sectional view of the distal end of the perfusion catheter of FIG. 9.

Referring now to FIGS. 9 to 11, a further alternative embodiment of a perfusion catheter system constructed in accordance with the principles of the present invention is described. Catheter system 90 comprises perfusion catheter 95 and stylet 125. Stylet 125 is constructed as described hereinabove.

Perfusion catheter 95 comprises inner shaft 96 having proximal end 97 and distal end 98. Proximal end 97 includes fitting 99 for coupling blood flow inlet port 100 of the perfusion catheter to an outlet of a cardiopulmonary bypass machine (not shown). Distal end 98 includes sealing member 101, curved region 102 having cardioplegia outlet ports 103, occlusion balloon 104 and blood flow outlet port 105. Lumen 106 (see FIG. 11) extends from blood flow inlet port 100 to blood flow outlet port 105. Outer shaft 107 is disposed for movement in the proximal and distal directions on inner shaft 96 and includes sealing member 108 on distal end 109 and locking ring 110 on proximal end 111. Locking ring 110 may be configured to engage optional threads 112 disposed on the exterior surface of inner shaft 96, and serves to lock outer shaft 107 in at a desired position relative to inner shaft 102.

Sealing member 101, preferably a toroidal balloon, and occlusion balloon 104, are coupled to inflation ports 113 and 114, respectively, via separate lumens 115 disposed within lumen 106 (see FIG. 11). Inflation ports 113 and 114 may be coupled to syringes (not shown) filled with an inflation medium, such as saline, to selectively inflate the balloons. Cardioplegia outlet ports 103 are coupled to cardioplegia inlet port 116 via lumen 117 disposed within lumen 106. Sealing member 108 may comprise a flange formed from an elastomeric or closed-cell foam material. Alternatively, sealing member 108 may comprise an inflatable toroidal balloon, in which case outer shaft 107 will include an inflation port and inflation lumen.

Perfusion catheter 95 preferably comprises a material, as described hereinabove, and includes a preformed metal alloy spring embedded in its thickness that flexes from a substantially straight shape, when perfusion catheter 95 is disposed over stylet 125, to a curved shape that conforms to the arch of the aorta, as shown in FIGS. 10. Sealing member 101 and occlusion balloon 104 may comprise a compliant, semi-compliant, or non-compliant material, and more preferably, sealing member 101 comprises a non-compliant or semi-compliant material, while occlusion balloon 104 more preferably comprises a compliant material. Sealing member 108 may comprise a non-compliant or semi-compliant balloon, or elastomeric or foam material.

Referring now to FIGS. 10A and 10B, when perfusion catheter 95 is positioned within a vessel, preferably aorta A, curved region 102 conforms to the curve of the aorta. Sealing member 101 is disposed within aorta A and is inflated to contact the interior surface of tissue T. Outer shaft is then translated in the distal direction so that sealing member 108 is disposed against the exterior surface of tissue T, and locking ring 110 is actuated to lock the outer shaft in a fixed position relative to inner shaft 96. If sealing member 108 is a balloon, it is inflated to bear against the opposite surfaces of the thickness of tissue T. If sealing member 108 is non-expandable, translation of sealing member 108 toward sealing member 101 causes the sealing members to bear against the opposite surfaces of the thickness of tissue T, thus providing a sutureless arteriotomy seal for perfusion catheter 95.

Operation of catheter system 90 is similar to that described with respect to FIGS. 4A to 4C. The aorta is first partially clamped to isolate a region in which the arteriotomy is to be performed, and perfusion catheter 95 is placed over stylet 125 so that the tip of the stylus extends out of blood flow outlet port 105. Sealing member 101 and occlusion balloon 104 are folded against the exterior of perfusion catheter 95 so as to minimize the insertion profile of the catheter. The perfusion catheter and stylet are disposed adjacent to the isolated region of the aorta, and the stylet is advanced to create a puncture in the vessel wall.

The perfusion catheter is then advanced over the distal end of the stylet with the stylet held stationary, so that curved region 102 reverts to its curved shape as the perfusion catheter is inserted into the aorta through the puncture. Sealing member 101 is inflated, and then sealing member 108 is advanced distally to contact and bear against the intervening thickness of the vessel wall. Alternatively, outer shaft 107 may be positioned relative to inner shaft 96 prior to inflation of the sealing member or members. Occlusion balloon 104 also is inflated using a suitable inflation medium, injected via inflation port 114, to occlude the aorta upstream of blood flow outlet port 105.

Stylet 125 is removed from lumen 106, and blood flow inlet port 100 is coupled to an outlet of a cardiopulmonary bypass machine to perfuse aorta A. Cardioplegia solution also may be injected through cardioplegia inlet port 116, lumen 117 and cardioplegia outlet ports 103 into the aortic root to stop the heart and perfuse the coronary arteries.

As a further alternative embodiment, perfusion catheter system 95 may omit lumen 117, cardioplegia outlet ports 103 and occlusion balloon 104. In this case, perfusion catheter 95 may include a tube (similar to tube 26 of the embodiment of FIG. 1) affixed to inner shaft 96, within sealing member 101, and over which sealing member 108 is slidably disposed. In this embodiment, a separate balloon catheter, such as balloon catheter 40 of FIG. 1, may be inserted through the tube to provide the occlusion and cardioplegia injection functions described hereinabove with respect to the embodiment of FIG. 1.

While preferred illustrative embodiments of the invention are described above, it will be apparent to one skilled in the art that various changes and modifications may be made therein without departing from the invention, and it is intended in the appended claims to cover all such changes and modifications which fall within the true spirit and scope of the invention.

What is claimed is:

1. A catheter system for use with a cardiopulmonary bypass machine to deliver oxygenated blood to a patient through an opening in a patient's vessel, the catheter system comprising:
   a catheter having a proximal end including a cardioplegia inlet port and a blood flow inlet port adapted to be coupled to a cardiopulmonary bypass machine to receive oxygenated blood, and a distal region including a cardioplegia outlet port in fluid communication with the cardioplegia inlet port and a blood flow outlet port in fluid communication with the blood flow inlet port;
   an occlusion balloon disposed in the distal region proximal to the blood flow outlet port and distal to the cardioplegia outlet port;
   a first sealing member disposed proximal to the cardioplegia outlet port, the first sealing member compressively engaging an interior lateral surface of a vessel wall; and
   a second sealing member disposed proximal and adjacent to the first sealing member, the second sealing member compressively engaging an exterior lateral surface of a vessel wall.

2. The catheter system of claim 1 wherein the catheter further comprises an outer shaft disposed for translation on an inner shaft, the first sealing member being disposed on the inner shaft and the second sealing member being disposed on the outer shaft.

3. The catheter system of claim 2 wherein the first sealing member comprises a first balloon, the inner shaft further comprising a first inflation port coupled to the first balloon.

4. The catheter system of claim 3 wherein the inner shaft further comprises:
   a second inflation port coupled in fluid communication to the the occlusion balloon.

5. The catheter system of claim 4 wherein the cardioplegia outlet port comprises a plurality of apertures disposed in the inner shaft proximal to the occlusion balloon and distal to the first sealing member.

6. The catheter system of claim 3 wherein the second sealing member comprises an elastomeric or foam flange.

7. The catheter system of claim 2 wherein the outer shaft further comprises a locking ring to lock the outer shaft at a desired position relative to the inner shaft.

8. The catheter system of claim 2 wherein a distal region of the inner shaft further comprises a pre-formed spring that biases the inner shaft to a curved shape that conforms to the vessel.

9. The catheter system of claim 2 further comprising a stylet having a sharpened distal end, the stylet configured to be inserted through a lumen of the catheter so that a distal end of the stylet extends from the blood flow outlet port.

10. The catheter system of claim 1 wherein the first and second sealing members comprise first and second balloons, the catheter further comprising first and second inflation ports, the first and second inflation ports coupled to the first and second balloons, respectively.

11. The catheter system of claim 10 wherein the first and second balloons have a toroidal shape.

12. The catheter system of claim 10 wherein the first and second balloons comprise a non-compliant material.

13. The catheter system of claim 1 wherein the catheter further comprises an inflation port coupled in fluid communication to the the occlusion balloon.

14. The catheter system of claim 13 wherein the occlusion balloon comprises a compliant material.

15. The catheter system of claim 13 wherein the cardioplegia outlet port comprises a plurality of apertures disposed proximal to the occlusion balloon and distal to the first sealing member.

16. The catheter system of claim 1 wherein the distal region further comprises a pre-formed spring that biases the distal region to a curved shape that conforms to the vessel.

17. The catheter system of claim 1 further comprising a stylet having a sharpened distal end, the stylet configured to be inserted through a lumen of the catheter so that a distal end of the stylet extends from the blood flow outlet port.

18. A method of perfusing oxyqenated blood from a cardiopulmonary bypass machine to a patient, comprising:
   providing a catheter having a proximal end including a cardioplegia inlet port and a blood flow inlet port and a distal region including a cardioplegia outlet port in fluid communication with the cardioplegia inlet port, a blood flow outlet port in fluid communication with the blood flow inlet port, first and second sealing members disposed proximally of the cardioplegia outlet port, and an occlusion balloon disposed between the cardioplegia outlet port and the blood flow outlet port;
   creating a puncture in a vessel wall having a thickness;
   inserting the catheter through the puncture so that the blood flow outlet port is aligned with an axis of the vessel;
   positioning the first sealing member to compressively engage an interior lateral surface of the vessel wall;
   positioning the second sealing member to compressively engage an exterior lateral surface of the vessel wall;
   inflating the occlusion balloon to occlude the vessel. proximally of the blood flow outlet port;
   coupling the blood flow inlet port to a cardiopulmonary bypass machine to receive oxygenated blood; and
   infusing the oxygenated blood into the vessel via the blood flow outlet port.

19. The method of claim 18 wherein creating the puncture in the vessel wall further comprises:
   inserting a stylet having a sharpened distal end through a lumen of the catheter so that a distal end of the stylet extends from the blood flow outlet port; and
   inserting the sharpened distal end of the stylet through the thickness of the vessel wall.

20. The method of claim 18 further comprising:
   coupling a source of cardioplegia solution to the cardioplegia inlet port; and
   infusing a cardioplegia solution into the aortic root via the cardioplegia outlet port.

21. The method of claim 18 wherein the first and second sealing members comprise first and second balloons and positioning the first and second sealing members further comprises inflating the first and second balloons.

22. The method of claim 18 wherein inserting the catheter through the puncture further comprises sliding the catheter distally off of the stylet while retaining the stylet stationary.

23. The method of claim 18 wherein providing the catheter further comprises providing a catheter having an inner shaft and an outer shaft, the first sealing member being disposed on the inner shaft, the second sealing member being disposed on the outer shaft, and positioning the first and second sealing members comprises translating the outer shaft relative to the inner shaft.

24. A method of perfusing oxygenated blood from a cardiopulmonary bypass machine to a patient, comprising:
   providing a catheter having a proximal end including a blood flow inlet port and a distal region including a blood flow outlet port in fluid communication with the blood flow inlet port and a pre-formed spring that biases the distal region to a curved shape that conforms to the vessel, and first and second sealing members;

creating a puncture in a vessel wall having a thickness;

inserting the catheter through the puncture so that the pre-formed spring causes the blood flow outlet port to become aligned with an axis of the vessel;

positioning the first sealing member to compressively engage an interior lateral of the vessel wall;

positioning the second sealing member to compressively engage an exterior lateral surface of the vessel wall;

coupling the blood flow inlet port to a cardiopulmonary bypass machine to receive oxygenated blood; and infusing the oxygenated blood into the vessel via the blood flow outlet port.

25. The method of claim 24 wherein creating the puncture in the vessel wall further comprises:

inserting a stylet having a sharpened distal end through a lumen of the catheter so that a distal end of the stylet extends from the blood flow outlet port; and inserting the sharpened distal end of the stylet through the thickness of the vessel wall.

26. The method of claim 24 wherein providing the catheter further comprises providing a catheter having an occlusion balloon disposed in the distal region, and occluding the vessel proximally of the blood flow outlet port comprises inflating the occlusion balloon.

27. The method of claim 24 further comprising:

coupling a source of cardioplegia solution to the cardioplegia inlet port; and infusing a cardioplegia solution into the aortic root.

28. The method of claim 24 wherein the first and second sealing members comprise first and second balloons and positioning the first and second sealing members further comprises inflating the first and second balloons.

29. The method of claim 25 wherein inserting the catheter through the puncture further comprises sliding the catheter distally off of the stylet while retaining the stylet stationary.

30. The method of claim 24 wherein providing the catheter further comprises providing a catheter having an inner shaft and an outer shaft, the first sealing member being disposed on the inner shaft, the second sealing member being disposed on the outer shaft, and positioning the first and second sealing members comprises translating the outer shaft relative to the inner shaft.

* * * * *